(12) United States Patent
Corl

(10) Patent No.: US 10,973,419 B2
(45) Date of Patent: *Apr. 13, 2021

(54) INTRAVASCULAR PRESSURE DEVICES INCORPORATING SENSORS MANUFACTURED USING DEEP REACTIVE ION ETCHING

(71) Applicant: Volcano Corporation, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 475 days.

This patent is subject to a terminal disclaimer.

(21) Appl. No.: 15/077,174

(22) Filed: Mar. 22, 2016

(65) Prior Publication Data
US 2016/0198958 A1    Jul. 14, 2016

Related U.S. Application Data

(63) Continuation of application No. 11/864,499, filed on Sep. 28, 2007, now Pat. No. 9,289,137.

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/6851* (2013.01); *G01L 9/0054* (2013.01); *G01L 19/143* (2013.01); *A61B 5/026* (2013.01)

(58) Field of Classification Search
CPC ........................ A61B 5/02154; A61B 5/0215
See application file for complete search history.

(56) References Cited

U.S. PATENT DOCUMENTS 3,350,944 A    11/1967  De Michele
3,724,274 A *  4/1973  Millar .................. A61B 5/0215
                                                    338/4
(Continued)

FOREIGN PATENT DOCUMENTS

JP    S56-172954    12/1981
JP    S61-168969    7/1986
(Continued)

OTHER PUBLICATIONS

["Micromachined silicon cantilever paddles with piezoresistive readout for flow sensing" by Su et al., Journal of Micromechanics and Microengineering, vol. 6, pp. 69-72, 1996.*
(Continued)

*Primary Examiner* — Kaylee R Wilson
*Assistant Examiner* — Jay B Shah

(57) ABSTRACT

An intravascular pressure sensor assembly is disclosed herein that is produced in part using photolithography and DRIE solid-state device production processes. Using DRIE production processes facilitates a number of features that could not be readily incorporated in sensor chips fabricated using mechanical saws. In accordance with a first feature, sensor chips are created with non-rectangular outlines. The sensor chip includes a widened portion that substantially abuts an inner wall of a sensor housing, and a cantilevered portion that is relatively narrow in relation to the widened portion. The non-rectangular outline of the sensor chip is formed using photolithography in combination with DRIE processing. In accordance with another feature, the sensor chip is positioned width-wise in the housing, thereby reducing a required length for the housing. In accordance with yet another feature, the sensor chip comprises one or more cutouts for receiving signal wires for connection to signal lead lines on the sensor chip. The outline of the sensor chip
(Continued)

and the cutouts are formed using photolithography in combination with DRIE processing.

24 Claims, 6 Drawing Sheets

(51) Int. Cl.
 *G01L 9/00* (2006.01)
 *G01L 19/14* (2006.01)
 *A61B 5/026* (2006.01)

(56) References Cited

U.S. PATENT DOCUMENTS

| | | | |
|---|---|---|---|
| 3,946,724 A * | 3/1976 | La Balme | A61B 5/0215 128/902 |
| 4,274,423 A | 6/1981 | Mizuno et al. | |
| 4,554,927 A | 11/1985 | Fussell | |
| 5,324,326 A | 6/1994 | Lubin | |
| 5,807,265 A | 9/1998 | Itoigawa et al. | |
| 6,062,089 A | 5/2000 | Ichihashi | |
| 6,167,763 B1 * | 1/2001 | Tenerz | A61B 5/0215 73/756 |
| 6,336,906 B1 | 1/2002 | Hammarstrom et al. | |
| 6,868,736 B2 * | 3/2005 | Sawatari | G01L 9/0042 73/800 |
| 6,976,965 B2 | 12/2005 | Corl et al. | |
| 8,048,063 B2 * | 11/2011 | Aeby | A61B 5/042 385/13 |
| 2003/0040674 A1 * | 2/2003 | Corl | A61B 5/0215 600/486 |
| 2003/0163052 A1 * | 8/2003 | Mott | A61B 5/0215 600/486 |
| 2005/0065592 A1 | 3/2005 | Holzer | |
| 2006/0137457 A1 | 6/2006 | Zdeblick | |
| 2008/0009750 A1 * | 1/2008 | Aeby | A61B 5/042 600/478 |

FOREIGN PATENT DOCUMENTS

| | | |
|---|---|---|
| JP | H09-187515 | 7/1997 |
| JP | H10-505269 | 5/1998 |
| JP | H11-511291 | 9/1999 |
| JP | 2004-525357 | 8/2004 |
| JP | 2007-078378 | 3/2007 |
| WO | WO 1996/007351 | 3/1996 |
| WO | WO 1996/037784 | 11/1996 |
| WO | WO 2005/000294 | 1/2005 |

OTHER PUBLICATIONS

"Emerging Technologies MEMS in medicine and biology" by Panescu, IEEE Engineering in Medicine and Biology Magazine, Sep./Oct. 2006, pp. 19-28.*
Arecco—Analysis and preliminary characterization of a MEMS cantilever-type chemical sensor; Master of Science Thesis; Mechanical Engineering Department Worcester Polytechnic Institute, 2003. (Year: 2003).*
International Search Report and Written Opinion of PCT/US08/77853 dated Nov. 28, 2008.
Japanese Patent Office, Office action for JP Application No. 2013-111062 dated Mar. 18, 2014, 8 pages.
European Patent Office, "European Search Report" for Application No. 08833223.4, dated May 27, 2014, 8 pages.
Japanese Patent Office, "Office Action" for Application No. 2013-111052, dated Nov. 12, 2015, 4 pages including translation.
"Microfabricated ultrasensitive piezoresistive cantilevers for torque mangetometry" by Brugger et al., Sensors and Actuators, vol. 73, pp. 235-242, 1999.
"Microfabrication of cantilever styli for the atomic force microscope" by Albrecht et al., Journal of Vacuum Science and Technoloy, vol. 8, 1990.

* cited by examiner

INTRAVASCULAR PRESSURE DEVICES INCORPORATING SENSORS MANUFACTURED USING DEEP REACTIVE ION ETCHING

CROSS-REFERENCE TO RELATED APPLICATION

This application is a continuation of U.S. patent application Ser. No. 11/864,499, filed Sep. 28, 2007, the entirety of which is hereby incorporated by reference herein.

AREA OF THE INVENTION

The present invention generally relates to the area of diagnostic medical equipment, and more particularly to diagnostic devices for identifying problematic blockages within coronary arteries by means of a pressure sensor assembly mounted at a distal end of a flexible elongate member such as a guidewire.

BACKGROUND

In the past two decades, innovations in the diagnosis of cardiovascular disease have expanded from external imaging processes to internal, catheterization-based, diagnostic processes. Diagnosis of cardiovascular disease has been performed through angiogram imaging wherein a radiopaque dye is injected into a vasculature and a live x-ray image is taken of the portions of the cardiovascular system of interest. More recently, however, diagnostic equipment and processes have been developed for diagnosing vasculature blockages and other vasculature disease by means of ultra-miniature sensors placed upon a distal end of a flexible elongate member such as a catheter, or a guidewire used for catheterization procedures.

One such ultra-miniature sensor device is a pressure sensor mounted upon the distal end of a guidewire. A particular example of such a pressure sensor is provided in Corl et al. U.S. Pat. No. 6,106,476, the teachings of which are expressly incorporated herein by reference in their entirety. The intravascular pressure sensor measures blood pressure at various points within a vasculature and facilitates locating and determining the severity of stenoses or other disruptors of blood flow within blood vessels. Such devices are commonly used to determine the effectiveness of an angioplasty procedure by placing the pressure sensor distal to a stenosis and measuring a pressure difference relative to the proximal pressure measured through a guiding catheter by traditional methods. A significant pressure gradient, for example greater than 30 mmHg, is indicative of a functionally significant blockage of the vessel.

A presently used manufacturing technique for manufacturing a solid-state pressure sensor for an intravascular pressure sensor wire relies upon a mechanical saw to shape the pressure sensor. In the known mechanically shaped devices, wafer thinning is an important step in fabricating a solid-state pressure sensor chip. Normally, pressure sensors are fabricated on or near a surface of a relatively thick supporting wafer of either silicon or glass. The supporting wafers are typically 400 µm or more in thickness, and the supporting wafers are robust and suitable for manual handling or handling by automated fabrication machinery. However, at a latter stage of the production process, it is necessary to thin the wafer to less than 100 µm, possibly as thin as 50 µm, to produce a device mountable within a coronary guidewire. The thin wafer is difficult to handle and subject to breakage or other damage in subsequent processing steps such as diamond saw dicing which cuts the wafer into tiny rectangular sensor chips that can be subsequently mounted in a guidewire.

The known fabrication process for pressure sensors using diamond saw dicing is fast, efficient, and therefore widely used. However, the diamond sawing is only capable of rendering simple "rectangular" device outlines.

Once the pressure sensor is mounted in a guidewire or similar device, it is subject to external stress arising from bending of the guidewire to access the coronary anatomy, or from differential thermal expansion of the various guidewire components. External stress on the pressure sensitive portion of the sensor chip can produce undesirable pressure artifacts. A guidewire containing a pressure sensor includes a housing that facilitates cantilever mounting of the sensor chip. The cantilever mounting arrangement ensures that surrounding guidewire structures do not exert external stress to the pressure sensitive region of the chip.

Deep reactive-ion etching (DRIE) is a highly anisotropic etch process for creating deep, steep-sided holes and trenches in solid-state device wafers, with aspect ratios of 20:1 or more. DRIE was originally developed for microelectromechanical systems (MEMS). However, DRIE is also used for producing other devices such as to excavate trenches for high-density capacitors for DRAM. DRIE is capable of fabricating 90° (truly vertical) walls.

SUMMARY OF THE INVENTION

The present invention comprises new intravascular pressure sensing devices, and methods of manufacturing such devices using DRIE to form such devices. Using photolithography and DRIE etching to pattern a miniature pressure sensor with a non-rectangular outline and internal cutouts facilitates a number of improved features in a coronary guidewire pressure measurement assembly.

Thus, an intravascular pressure sensor assembly is disclosed herein that is produced in part using DRIE solid-state device production processes. The assembly includes a flexible elongate member, such as a guidewire, including a proximal and a distal end. The assembly also includes a housing mounted at the distal end of the flexible elongate member and a sensor chip that is contained within the housing.

As noted above, using DRIE production processes facilitates a number of features that could not be readily incorporated, if at all, in sensor chips fabricated using mechanical saws. In accordance with a first feature, sensor chips are created with non-rectangular outlines. Thus, in accordance with illustrative examples, the sensor chip includes a widened portion that substantially abuts an inner wall of the housing, and a cantilevered portion that is relatively narrow in relation to the widened portion. The cantilevered portion includes a diaphragm comprising at least one piezoresistive element for sensing pressure. The non-rectangular outline of the sensor chip is formed using photolithography in combination with DRIE processing.

In accordance with another feature, the sensor chip is positioned width-wise in the housing, thereby reducing a required length for the housing. The outline of the sensor chip is formed using photolithography in combination with DRIE processing.

In accordance with yet another feature, the sensor chip comprises one or more cutouts for receiving signal wires for connection to signal lead lines on the sensor chip. The cutouts are formed using photolithography in combination with DRIE processing.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

DETAILED DESCRIPTION OF THE DRAWINGS

The guidewire mounted pressure sensor and its method of production are based upon the use of DRIE to form the solid-state sensor rather than previously used mechanical saws. Extreme stress applied to the sensor chip substrates in the course of saw dicing can create subtle damage to the sensors, permanently degrading their performance or rendering them vulnerable to premature failure. Using DRIE leads to a number of new pressure sensor designs for intravascular applications wherein the sensor is mounted at a distal end of a pressure measuring coronary guidewire.

The DRIE method for microelectronic production is capable of etching an arbitrary pattern into a surface of a silicon wafer according to a pattern defined by photolithography. The DRIE process on a silicon substrate produces nearly vertical walls having a depth of 100 µm or more. In fact, the DRIE-based etching can be used to etch completely through a 400 µm thick wafer. Photolithography and DRIE can etch patterns with ~1 µm precision and create features with dimensions of 1 µm or less. DRIE is widely used in silicon wafer processing. When applied to manufacturing intravascular pressure sensors, the DRIE approach facilitates fabricating pressure sensors that are ideally suited for mounting at a distal end of a coronary guidewire.

The following is a listing of improvements arising from using DRIE in fabricating pressure sensors for coronary guidewires:
- a non-rectangular sensor substrate facilitates cantilevered support of the delicate pressure sensitive region of the sensor chip;
- a non-rectangular sensor outline facilitates extremely compact sensor mounting in the tip of a guidewire (by re-orienting the sensor substrate); and
- a set of precision cutouts in a pressure sensor facilitates employing a simplified arrangement for attaching wires to sensor leads and providing strain relief for the lead wire attachments.

Other potentially useful manufacturing features arise from use of a DRIE approach to form the sensor assembly of a pressure sensor wire. For example, the DRIE manufacturing approach facilitates production of multiple sensor chips simultaneously as a sheet. The individual sensors chips are attached to the sheet via tabs. After fabricating the set of sensor chips within the sheet, the tabs are broken to detach the individual chips from the sheet. A variety of attachment modes are possible, including simple ones that are broken by merely flexing the tab, and more complex tabs that are broken by squeezing an attachment structure. The tabs, in each case, are formed through photolithographic patterning and DRIE in a way to ensure that detaching the sensor chips from their silicon wafer support framework does not damage the sensor chips.

Figure 1:
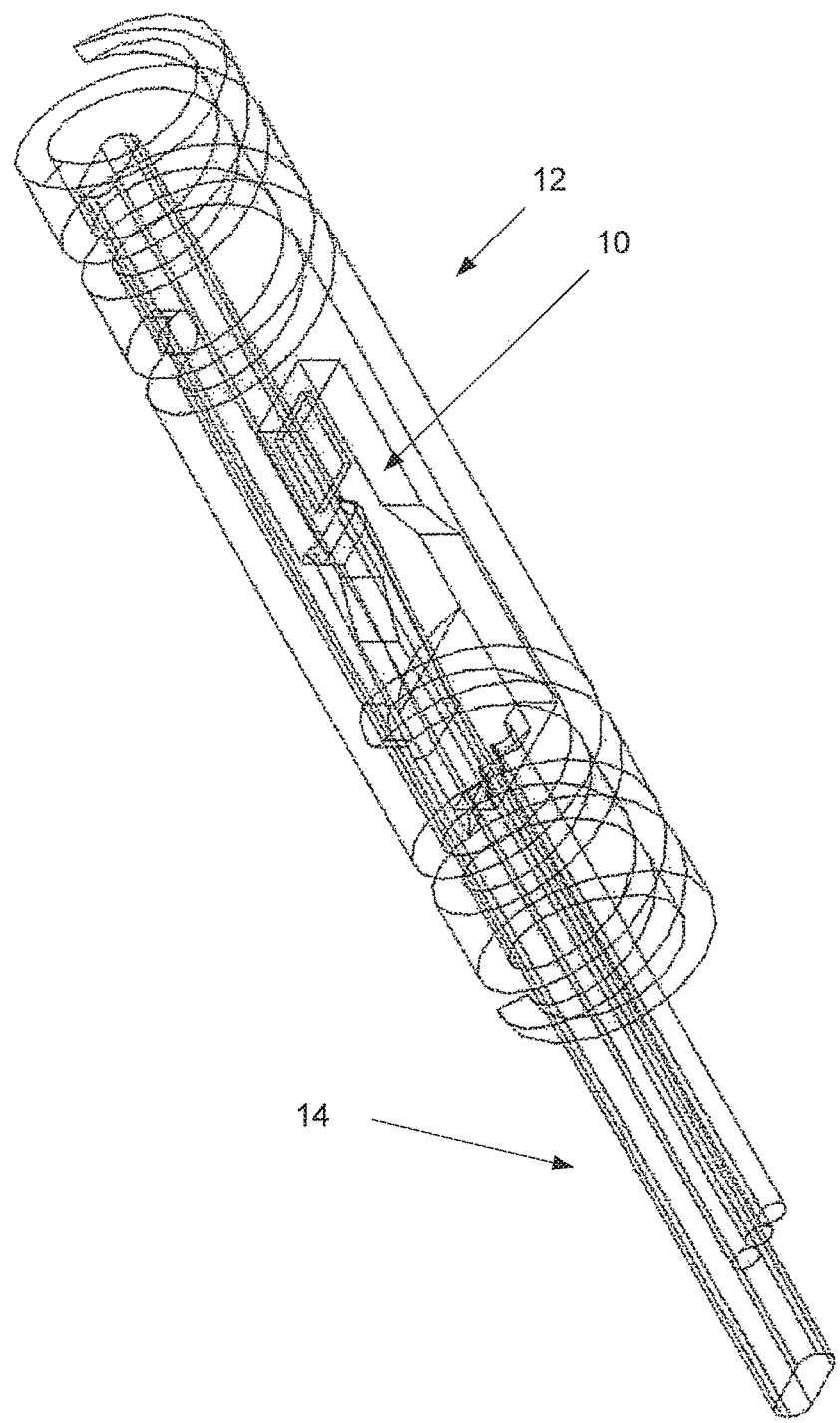
FIG. 1 is a transition housing of an exemplary pressure sensor guidewire including a pressure sensor assembly.

Turning to FIG. 1, a distal transition housing of an exemplary intravascular pressure sensing guidewire is depicted that contains a pressure sensor embodying the DRIE fabrication approach. In the illustrative embodiment, a pressure sensor chip 10 is securely mounted within a transition housing, typically located at a coil-to-coil transition near the distal end 12 of a pressure sensor guidewire 14. The housing 12 maintains a relatively constant outer profile in the region containing the pressure sensor chip 10. Also, it is noted that a cantilevered portion of the sensor chip 10 has a relatively smaller width than a lead portion to which a set of pressure sensor signal lead wires are coupled. In accordance with illustrative embodiments described herein below, the sensor chip 10 is fabricated using DRIE processing to provide an outline of virtually any desired shape—including chips having curved outline edges. A number of structural enhancements, as well as improved manufacturing methods, facilitated by DRIE processing of a silicon wafer to provide a set of pressure sensor chips (e.g., chip 10) are described herein below with reference to the figures.

Figure 2:
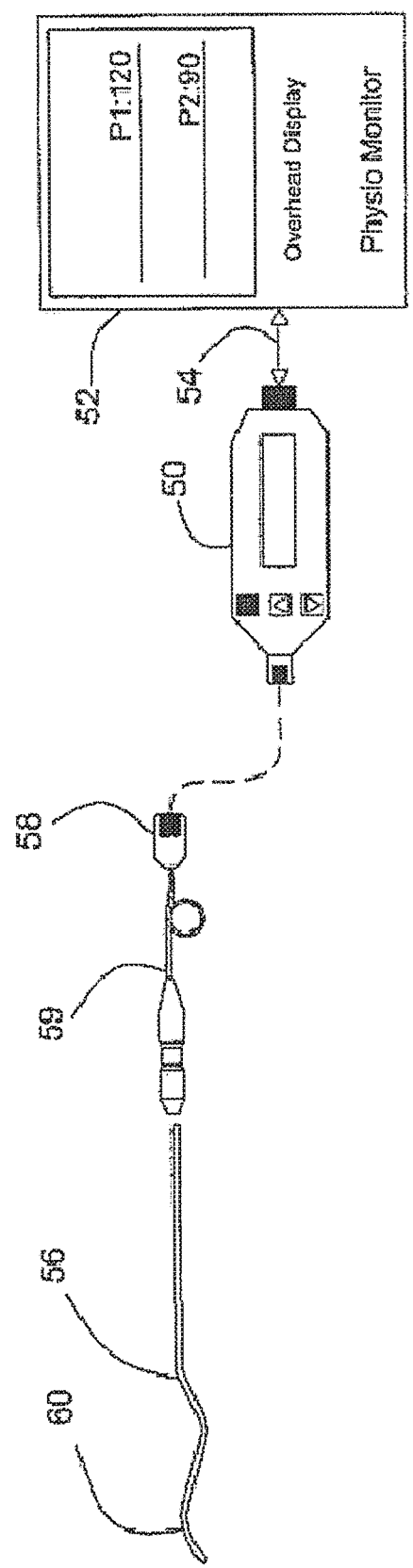
FIG. 2 is a schematic drawing depicting an exemplary connection scheme between a diagnostic pressure sensing guidewire and a physiology monitor in accordance with an exemplary operating environment for a solid-state pressure sensor embodying the present invention.

An exemplary pressure sensor assembly is incorporated into a pressure sensing guidewire and signal processing system generally described herein below with respect to FIG. 2. The exemplary system includes a silicon pressure sensor mounted upon a guidewire. An example of such a guidewire-mounted silicon pressure sensor is disclosed in Corl et al. U.S. Pat. No. 6,106,476, the contents of which are incorporated herein by reference in their entirety including any references contained therein. It is stressed that the intravascular pressure sensor system depicted in FIG. 2 is merely exemplary. The pressure sensor chips and the methods for manufacturing such chips described herein can be incorporated into virtually any intravascular pressure sensing assembly.

With continued reference to FIG. 2, in an exemplary embodiment of a system including pressure sensor chips of the type described herein, a signal conditioning device 50 connects to a physiology monitor 52 via a five line connector cable 54. The five line connector cable 54 includes a pair of excitation signal lines driven by the physiology monitor 52. The excitation signal lines are driven as a differential voltage pair at, by way of example, 2.4-11 Vdc, 2.4-8 Vrms sine wave (1 kHz to 5 kHz), or 2.4-8 Vrms square wave (dc to 5 kHz). Examples of physiology monitors include: all hemodynamic instruments with pressure sensor ports meeting American National Standards Institute ("ANSI")/AAMI BP22-1994; models RM-6000, RMC-2000, RMC-3100, Lifescope-S, RMC-1100, marketed by Nihon Kohden America, Inc. of Foothill Ranch, Calif.; models EP-1102 and EP-1600, marketed by the NEC Corporation of Tokyo, Japan; and models MCS-5500, MCS-7000, DS-3300, marketed by Fukuda Denshi of Tokyo, Japan.

The five line connector cable 54 includes a pair of differential output signal lines. The output signal lines are driven by the signal conditioning device 50's output digital to, analog converters (discussed further herein below). The differential output signal, by way of example, operates at 5 $\mu$V/V/mmHg. An operating range of −150 $\mu$V/V to 1650 $\mu$V/V therefore represents a sensed pressure range of −30 to 330 mmHg. An exemplary resolution (minimum step) for the differential output signal is 0.2 mmHg. The fifth line of the five line connector cable 54 carries a ground signal. Thus, all signal/power requirements for the signal conditioning device 50 are met by the standard five-line output of the physiology monitor 52.

On the patient side, the signal conditioning device 50 couples to a replaceable guidewire 56 via a connector 58 and corresponding static cable 59. The guidewire 56 includes, by way of example, a proximal shaft (also referred to as a hypo tube) including a core wire. The core wire extends from the distal tip of the guidewire to the proximal (connector) end of the guidewire 56 and serves at the backbone for the guidewire 56. In accordance with illustrative examples, a pressure sensor assembly is mounted at the distal tip of the guidewire 56 (as well as other locations such as a transition point on the guidewire that is several centimeters from the tip).

The connector 58 couples a set often lines in the static cable 59 carrying signals between the replaceable guidewire 56 and the signal conditioning device 50. A first set of five lines of the connector 58 is utilized to generate and receive pressure sensor-related signals. A second set of five lines of the connector 58 concerns an interface to a guidewire sensor's characterization electrically erasable programmable read-only memory ("EEPROM") mounted on the static cable 59 that stores a set of values relating to characteristics of a mounted sensor.

With regard to the second set of five lines of the connector 58, four of the five lines (the fifth line is not used) of the ten-line connector 58 facilitate reading characterization data from an EEPROM carried on the static cable for a guidewire-mounted sensor device 60, which is by way of example a pressure sensor. The EEPROM includes temperature compensation, gain, and offset values used by the signal conditioning device 50 to process the sensed signals from the sensor device 60. A power and ground line are provided by the signal conditioning device 50 to the EEPROM via the connector 58. A clock and data line for reading the EEPROM's data make up the final two lines.

The first set of five lines associated with the connector 58 includes a voltage reference line that is, by way of example, connected to each of two pressure sensing silicon resistive sensor elements on guidewire-mounted pressure sensor 60. The remaining four lines comprise two sets of excite/sense signal pairs. In an embodiment of the invention, a first current flows on a first, shorted, excite/sense pair of lines. A second current, separately adjustable with regard to the first current, flows on a second, shorted, excite/sense pair of lines of the connector 58. In the configuration of FIG. 2, the first and second currents pass through the first and second resistive sensor elements of the pressure sensor 60 mounted upon the distal end of the replaceable guidewire 56. A pressure sensing circuit including the resistive sensor elements is completed by connecting the remaining two terminals of the resistive sensor elements to the voltage reference line.

In operation, the electrical sensory circuit functions as follows. The silicon resistors on the pressure sensor 60 are pressure sensitive. In a particular embodiment having a pair of resistive elements, in response to a change in pressure one element increases resistance and a second element decreases resistance. For example, in an embodiment of the present invention each resistive element has a pressure sensitivity (at 100 mmHg, 25 degrees Celsius) of 15-35 $\mu$Ohms/Ohm/mmHg. By applying a steady current through the resistive elements, pressure changes result in changes in resistance that in turn result in voltage changes across the resistive sensor elements.

A common voltage reference, from which voltages across the first and second resistive elements are measured, is established by connecting a first terminal of each of the pair of resistive sensor elements of the sensor 60 to the common reference voltage provided by the signal conditioning device 50. A differential amplifier within signal conditioning device 50, via the excite/sense lines, senses a voltage difference corresponding to the voltages at the second terminal of each resistive sensor element to establish a voltage difference signal. An analog-to-digital converter ("ADC") within the signal conditioning device 50 converts the amplified analog voltage difference signal into a digital value. The digital value is received by the processor and filtered (e.g. finite impulse response filtered, or "FIR" filtered) in a known manner to render a filtered digital pressure value based upon prior calibration of the sensor 60. The filtered digital pressure value is then utilized to drive a digital input to a pair of output digital-to-analog converters ("DACs"). The pair of output DACs renders a differential output signal corresponding to an output signal transmitted on the cable 54 to the physiology monitor 52.

The drive current for each of the sensor 60's silicon resistive elements is, by way of example, 30 to 90 $\mu$A DC current, and the resistance value for each of the resistive elements is approximately 2500 ohms.

The silicon resistive elements, for example, have temperature sensitivities ranging from about 2.0 to 3.6 mOhm/Ohm/degree C. Because the temperature sensitivities of the resistive elements are not guaranteed to be identical, at least one of the two excitation lines carries an independently adjustable current to facilitate temperature compensation of the pressure sensor as well as, perhaps other characterization-based adjustments applied by the signal conditioning device to provide accurate pressure sensor readings. The separate sensor drive currents facilitate compensating for differences in changes to resistance in the sensor elements over the range of operating temperatures of the sensor 60. Temperature compensation is achieved by adjusting the excitation current driven on at least one of the two excitation lines to the pressure sensor such that the change in voltage across the sensor elements is substantially the same (i.e., within an acceptable error limit) throughout the entire range of operating temperatures.

It is noted that the above-described line composition for the cable connector 58 is exemplary. The sensor to which the signal conditioning device 50 is attachable and the composition of the lines between the sensor and signal conditioning device 50 vary in accordance with design considerations and functional requirements associated with alternative embodiments of the invention.

Figure 3A:
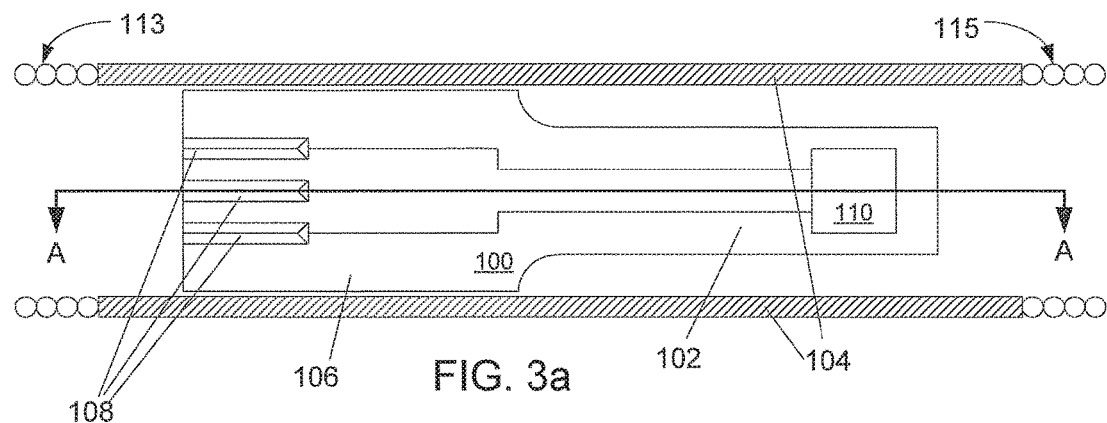
FIGS. 3a-d comprise multiple cross-sectional views of a housing containing a pressure sensor chip fabricated using photolithography and DRIE processes to produce chip shape features.

Turning now to FIG. 3a, a schematic diagram illustratively depicts the transition portion of a pressure sensor guidewire including a housing and a sensor chip. The transition is typically located approximately 3 cm proximal to the distal tip of a pressure sensing guidewire of the type depicted in FIG. 2, at the transition between a radiopaque tip coil and a radiolucent proximal coil. The diagram in FIG. 3a illustratively depicts a new sensor chip assembly facilitated by applying DRIE manufacturing procedures to production of a pressure sensor chip for use in an intravascular pressure sensing guidewire of the type depicted in FIGS. 1 and 2. In the illustrated example, a pressure transducer chip 100 includes both cantilever and mounting features defined in the outline of the chip 100. In particular, a cantilevered portion 102 of the mounted chip 100 resides relatively free-standing within a housing wall 104 located near the distal end of a pressure guidewire. Strain relief is thus provided by a widened portion 106 of the chip 100 having outer edges that are sized to abut the housing wall 104 and thus enable maintaining the cantilevered portion 102 in a free-standing position in relation to the relatively rigid housing wall 104 and a flattened portion of a core wire 107 (see, FIG. 3b). A space between the cantilevered portion 102 and the wall 104 is filled with air, liquid, or a highly elastic material (e.g., a low durometer silicone elastomer such as MED-4905, MED 4930, or similar from NuSil Technology LLC of Carpinteria, Calif.). The transition from the widened portion 106 to the cantilevered portion 102 is achieved by DRIE manufacturing processes wherein etching along a non-rectangular outline of the chip 100 achieves a very precise vertical etch along a defined outline for the chip 100. The vertical etch proceeds completely through at least the final thickness of a substrate from which the chip 100 is formed.

The widened portion 106, in addition to providing structural stability with regard to positioning the chip 100 within the space defined by the housing wall 104, may include a set of grooved lead attachment structures 108 to which trifilar wires 105 (see, FIG. 3b) comprising a set of three pressure sensor signal wires (not shown) are attached. In alternative embodiments the widened portion 106 includes flat contact regions to which the signal wires are attached. The cross-sectional view of FIG. 3a also includes a proximal coil section 113 and a radiopaque (platinum/iridium) distal coil section 115.

The cantilevered portion 102 includes a diaphragm 110 of known construction. By way of example, a vacuum-filled chamber is formed by etching a well or depression in a silicon wafer, then bonding that first silicon wafer to a second silicon wafer under vacuum. Subsequently, the first silicon wafer is thinned by grinding and etching in a known manner to leave just a thin membrane of silicon, the diaphragm 110, covering the pressure reference chamber. Silicon resistors implanted in the diaphragm prior to the wafer bonding stage now become pressure sensitive by virtue of their inherent sensitivity to strain created by pressure induced flexure of the thin diaphragm. Placement and orientation of the resistors according to well established principles can produce resistive elements having either positive or negative response to applied pressure.

Figure 3B:
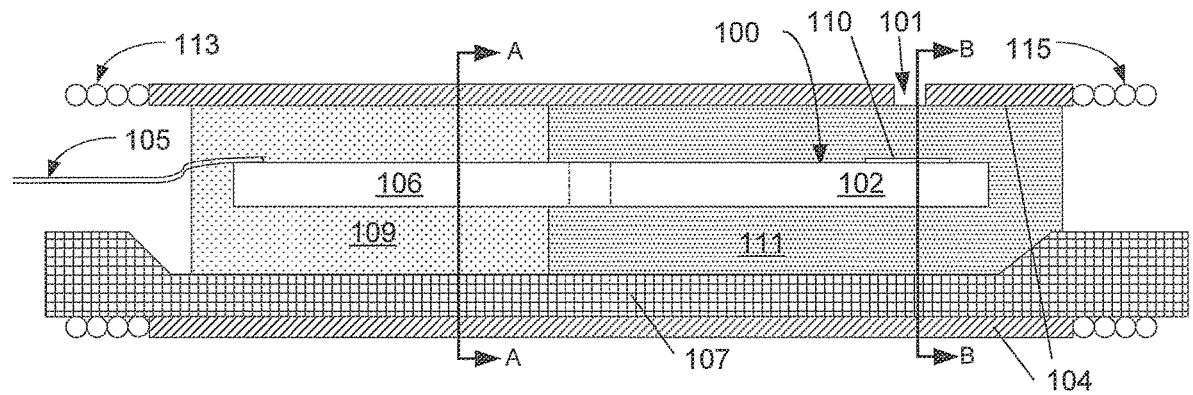

Turning to FIG. 3b, a cross-sectional view (taken along line AA of a transition housing portion for which a first cross-section is provided in FIG. 3a) depicts the transition region of the pressure guidewire containing the sensor chip 100. In the illustrated cross-sectional view, the chip 100 is generally spaced within the housing wall 104. An opening 101 in the housing wall 104 allows a fluid (e.g., blood) to exert pressure upon the diaphragm 110. In the illustrated embodiment, the widened portion 106 is held firmly in place by glue or any other suitable holding material 109 (even a silicon elastomer). The core wire 107 is flattened in the region of the housing to provide spacing from the chip 100, and more particularly the free-standing cantilevered portion 102 of the chip 100. A space 111 surrounding the cantilevered portion 102 comprises air, liquid, or highly elastic material (e.g., low durometer silicone elastomer). A transition from the relatively wide portion 106 to the relatively narrow portion 102 is shown via ghost lines on the chip 100. The core wire 107 is soldered or welded to the housing wall 104. The chip 100 is held in place by a holding material 109 within a portion of the housing containing the widened portion 106 which constitutes the portion of the chip 100 in contact with the housing wall 104. In addition, the cross-sectional view includes one of the trifilar wires 105 which connects to a contact for one of three leads to piezoresistive elements on the diaphragm 110.

Figure 3C:
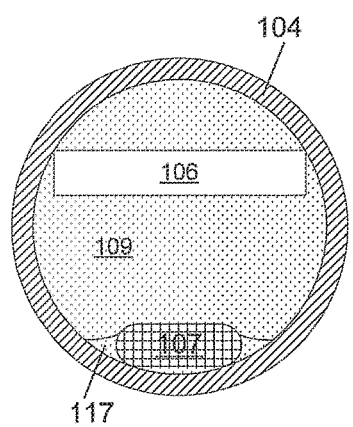

Turning to FIG. 3c, a cross-sectional view (taken along line AA of a transition housing portion for which a second cross-section is provided in FIG. 3b) depicts the widened portion 106 within the housing wall 104. The view also shows the flattened core wire 107 and solder 117. The holding material 109 fills the remaining portion of the cross-section.

Figure 3D:
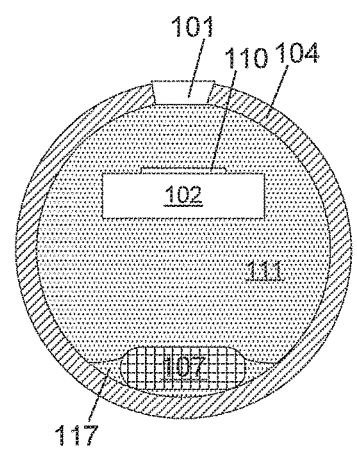

Turning to FIG. 3d, a cross-sectional view (taken along line BB of a transition housing portion for which a second cross-section is provided in FIG. 3b) depicts a cantilevered portion 102 of the chip 100. In contrast to the cross-section depicted in FIG. 3c, the view depicts the free-standing position of the cantilevered portion 102 of the chip 100 surrounded by the space 111 containing a material that conveys blood pressure via the opening 101.

Figure 4:
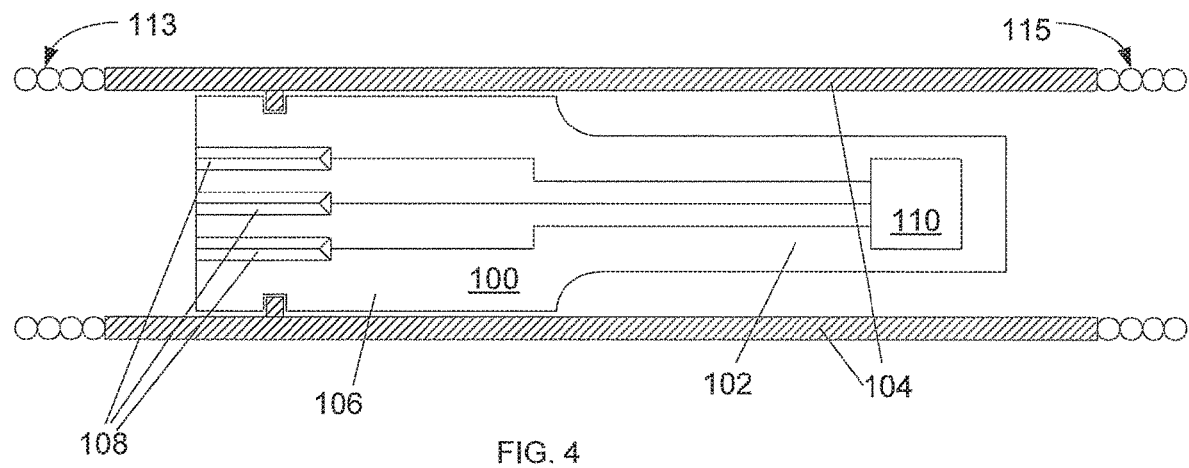
FIG. 4 illustratively depicts a cross-sectional view of a housing containing a pressure sensor chip having an alternative sensor chip profile wherein a pair of notches are provided.
Figure 5:
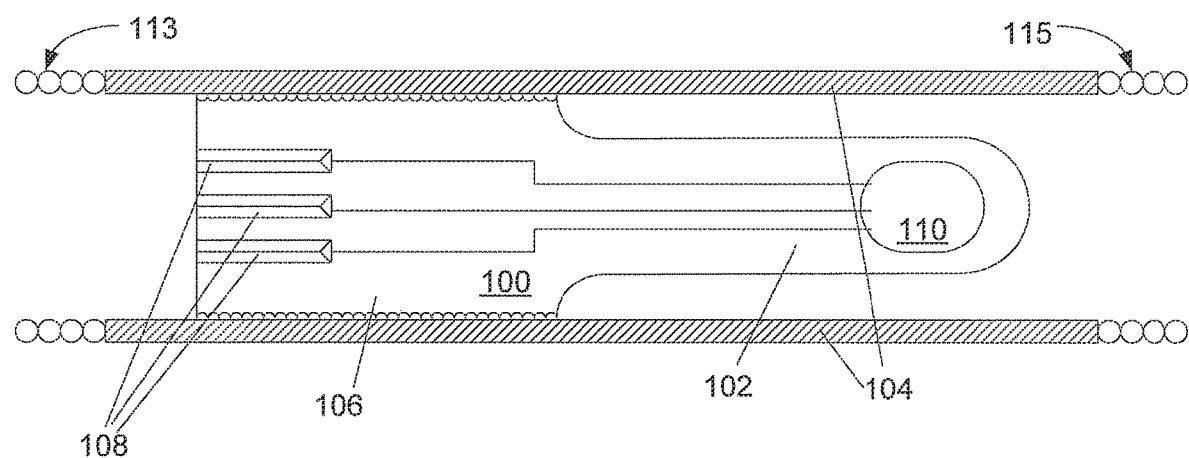
FIG. 5 illustratively depicts a cross-sectional view of a housing containing a pressure sensor chip having a textured profile along the edges of a widened portion of the sensor chip.

Turning to FIGS. 4 and 5, chip profile features facilitated by DRIE processing are presented that improve placement and/or bonding the sensor chip within the distal housing of a pressure guidewire. FIG. 4, presents an alternative sensor chip profile wherein a pair of notches are provided in the etch outline of the sensor chip 100. The notches are sized and positioned to correspond to a complimentary bead formed within the housing wall 104. After positioning the chip 100 within the housing, adhesive (not shown) is placed along the chip/housing wall borders to secure the chip 100 within the housing wall 104.

Turning to FIG. 5, an alternative sensor chip profile is illustrated. In the illustrative embodiment, the outline of the cantilevered portion 102 is curved. The diaphragm 110 is also curved inasmuch as the well of the diaphragm is curved (as opposed to rectangular). This non-rectangular shape for the well is facilitated by conventional photolithography and etching techniques. Yet another feature of the chip depicted in FIG. 5 is a textured edge along sides of the widened portion 106. The textured edges are formed through a photolithographic design in combination with DRIE processing to create an edge of arbitrary shape.

Figure 6:
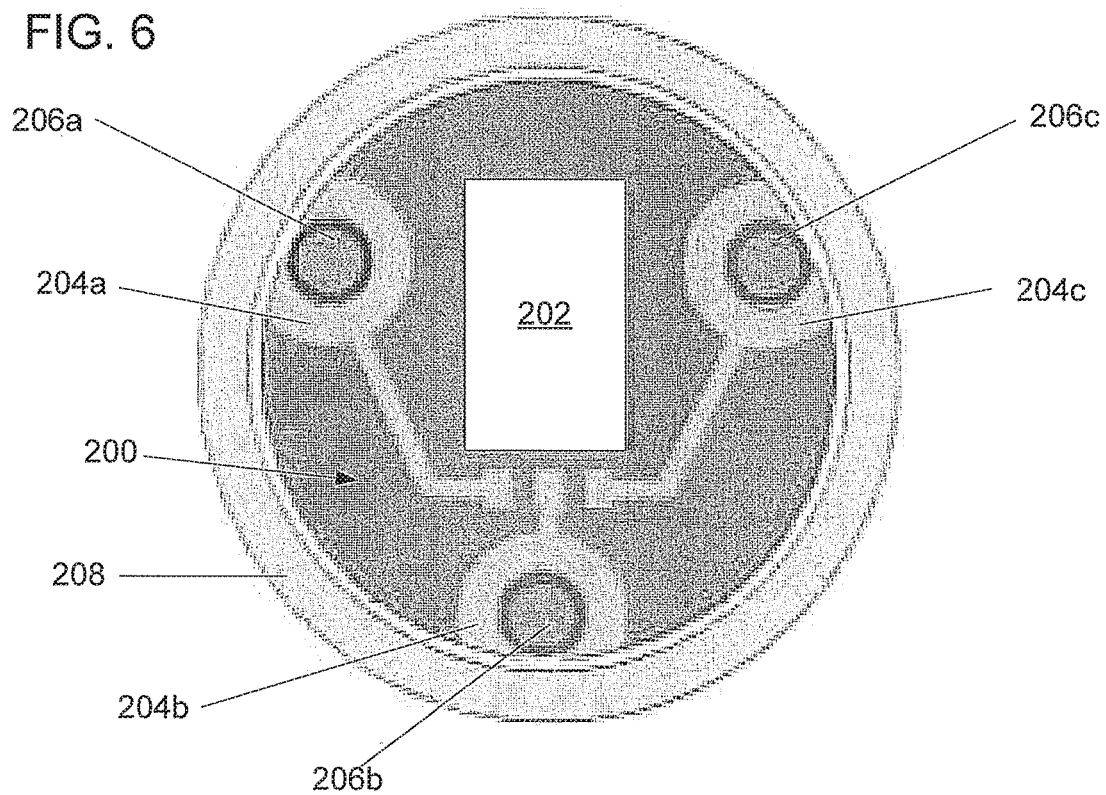
FIGS. 6 and 7 illustratively depict a very small disk-shaped pressure sensor chip that is mountable width-wise within a housing of a pressure sensing guidewire.

DRIE processing, in particular the ability to create pressure sensor chips having arbitrary outlines using photolithographic designs of virtually any shape in combination with DRIE, facilitates a sensor chip arrangement within a pressure guidewire distal tip having a space-limited cross-section. Turning to FIG. 6, a very small disk-shaped pressure sensor chip is depicted that is mountable width-wise (as opposed to lengthwise as shown in the embodiments depicted in FIGS. 3-5) within a housing of a pressure sensing guidewire with inner walls having a generally complimentary profile. In the chip designs depicted in FIGS. 3-5, the pressure sensor chip occupies a length of 500 to 1500 μm within the housing. The housing itself is about 2-4 mm long. Proximal and distal coils are soldered or glued to an outside of the housing (see, ghost lines of coil in FIG. 1) further extending the rigid length of the housing. The rigid section created by the coil, often 6 mm or more in length, compromises vascular accessibility. The pressure sensor chip design, and its orientation within the housing of a guidewire's distal tip, enables the pressure sensor chip to occupy roughly 100 μm of length along an axis of a guidewire. Furthermore, the exemplary disk shaped pressure sensor ship is mountable within a housing having a rigid length of 2 mm or less.

In accordance with the alternative embodiment of a sensor chip and housing-mounting arrangement depicted in FIG. 6, a generally disk-shaped sensor chip 200 has a circular outline that matches a cross-sectional space defined by a wall 208 of a screw tip housing for a pressure guidewire. It is noted that while a disk-shaped chip is presented in the illustrative embodiment, alternative shapes, including rectangular chips are contemplated in alternative embodiments. DRIE processing not only facilitates shaping of the outline of the pressure chips, DRIE processing also facilitates creating features on the sensor chip relating to the pressure transducer and electrical connections. These aspects of sensor chips manufactured using DRIE processing are discussed further herein below.

The structure of a diaphragm 202 on the chip 200 is substantially the same as the diaphragm of the devices depicted in FIGS. 3-5. In contrast to the pressure chip devices described herein above, the design depicted in FIG. 6 includes contacts 204a, 204b, and 204c spaced proximate the diaphragm 202. The chip 200 furthermore includes cutouts 206a, 206b and 206c to receive and anchor three electrical leads of the trifilar. A set of lead lines from the contacts 204a, 204b, and 204c signally couple the three wires of the trifilar to contacts of the piezoresistive elements formed on the diaphragm 202. In an exemplary embodiment, during manufacture the trifilar wires are passed through their respective cutouts 206, secured in place with glue (or simply mechanically captured by the cutouts 206), trimmed flush with the sensor chip surface, then soldered to establish a structurally secure electrical connection. In an embodiment wherein the sensor chip is placed at the tip of a guidewire, the face of the guidewire is covered with a soft silicone cap to insulate the electrical connections and to protect the sensor from impact. Exemplary tip configurations are described herein below with reference to FIGS. 9 and 10.

When generated in bulk with other sensor devices on a single silicon wafer, the pressure sensor chip devices are attached to the silicon wafer framework by a breakable tab. In an exemplary embodiment, the breakpoint of the breakable tab is positioned inside a generally continuous circular cross-section. When individual sensor chips are detached from the silicon wafer framework, a stump that remains after the tab is broken is positioned fully within a circular cross-section defining the general outline of the pressure sensor chip. The stump therefore will not interfere with placing the chip within a guidewire housing.

Figure 7:
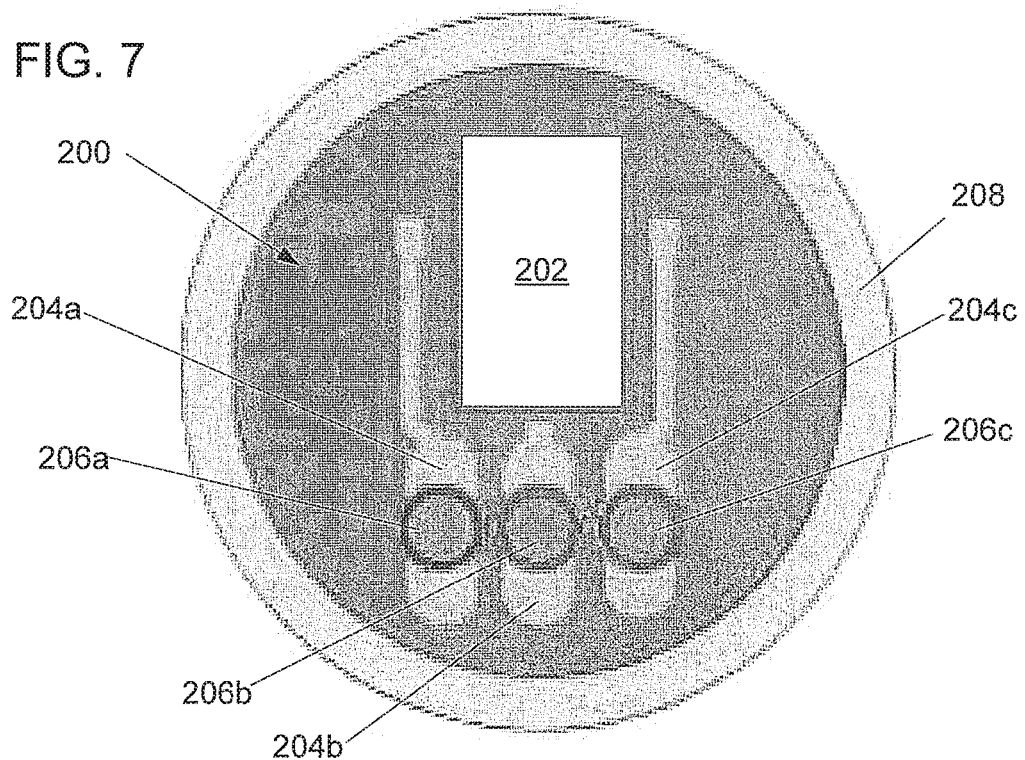
Figure 8:
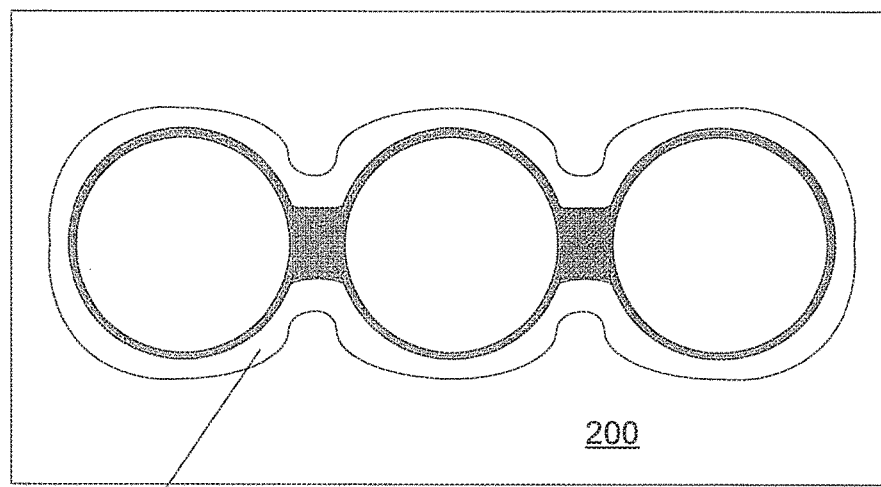
FIG. 8 illustratively depicts an alternative cutout (slot), to the ones depicted in FIG. 7, that includes a single slot through which wires of a trifilar pass.

Turning to FIG. 7, an alternative connection scheme places the contacts 204 and cutouts 206 adjacent to one another on the generally circular sensor chip 200. Alternatively, the three adjacent cutouts 206a, 206b, and 206c of FIG. 7 can be merged into a precisely shaped single cutout 206 within the chip 200 as shown in FIG. 8, to receive and support the bonded trifilar wire assembly. During manufacture, the separated leads of the trifilar pass through the cutouts 206a, 206b, and 206c in the case of the embodiment depicted in FIG. 7 or the bonded trifilar cable passes through the single cutout 206 shaped as a slot depicted in FIG. 8. Thereafter, the wires are trimmed flush with the surface of the chip 200 and then soldered. The precise shaping of the cutouts is provided by photolithography and DRIE processing.

Figure 9:
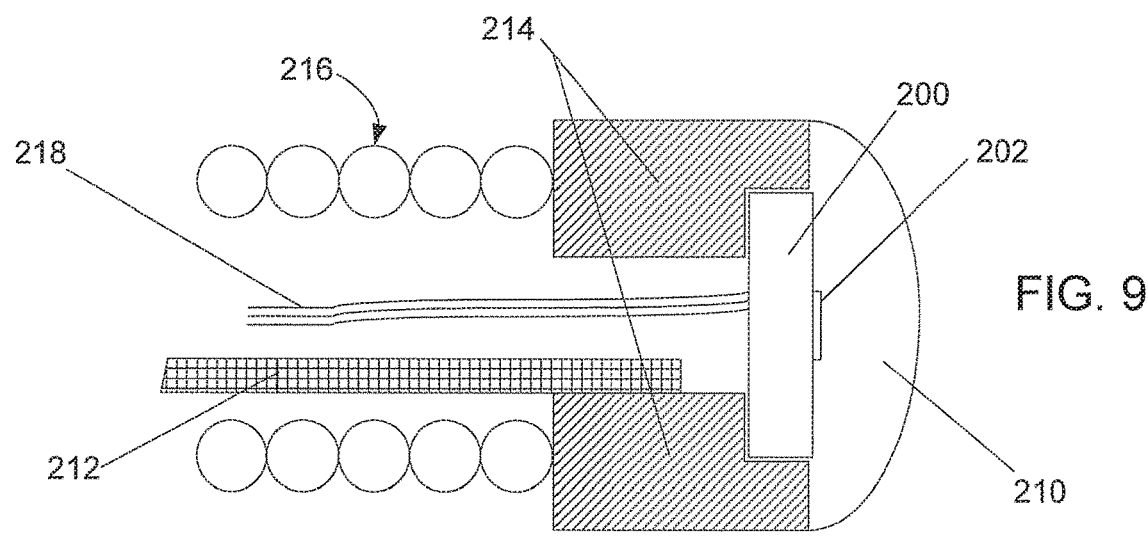
FIGS. 9 and 10 illustratively depict exemplary tip-mounted pressure sensor assemblies that utilize a width-wise mounted sensor chip such as the ones depicted in FIGS. 6 and 7.
Figure 10:
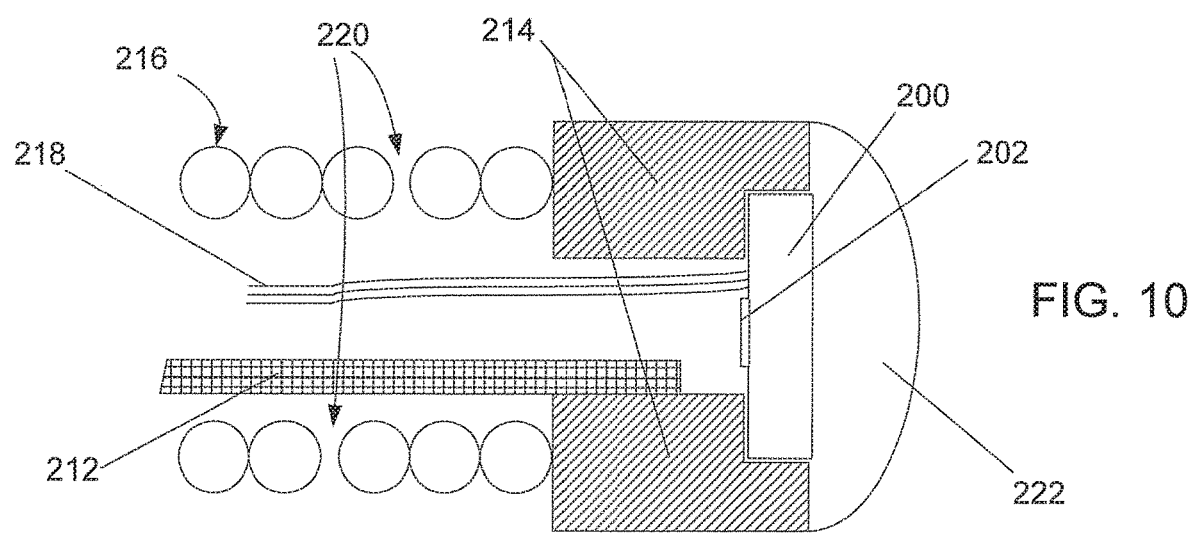

Turning to FIGS. 9 and 10, two exemplary pressure guidewire tip arrangements are illustratively depicted. Each is based upon the pressure sensor designs depicted, by way of example, in FIGS. 6, 7, and 8. Thus, both designs reduce a relatively long, stiff portion of a guidewire (transition housing section) containing the pressure sensor to a much shorter tip housing containing the pressure sensor.

In the embodiment depicted in FIG. 9, the diaphragm 202 is covered by a highly elastic material 210 (e.g., a soft silicone elastomer dome) that transmits an applied pressure at the guidewire's tip to the encapsulated pressure sensor's diaphragm 202. An example of such highly elastic materials is a low durometer silicone elastomer such as MED-4905, MED 4930, or similar from NuSil Technology LLC of Carpinteria, Calif. The applied pressure causes a change in the resistance of the piezoresistive elements on the surface of the diaphragm 202, and the resulting change in resistance is translated into a change in voltage across the piezoresistive elements. The exemplary embodiment depicted in FIG. 9 includes a flattened/tapered core wire 212 that is soldered to a housing 214 that supports the sensor chip 200. The housing 214 is also fixedly attached to the head of the guidewire coil 216 in any of a number of ways including soldering, gluing, or even screwing the housing 214 onto the tip coil. The wires of a trifilar 218 are attached, for example, according to either of the schemes depicted in FIG. 6, 7, or 8.

In the alternative embodiment depicted in FIG. 10, the diaphragm 202 is exposed to an applied pressure from within the housing 214. In this embodiment, fluid is allowed to pass through one or more openings 220 of the guidewire coil 216. A pressure is therefore applied to an exposed surface of the diaphragm 202. In this alternative embodiment, there is no need for cutouts since the contacts 204 are on the surface of the chip 200 that faces the wires of the trifilar 218. However, DRIE patterning may be used to create a receptacle (either partial or fully through the sensor) for the trifilar wire to ensure proper placement and to provide mechanical support and strain relief for the electrical connections. Since the diaphragm is not exposed on the outwardly facing surface of the chip 200, a relatively rigid (in comparison to the material 210 in FIG. 9) material 222 (e.g., Epo-Tek 301 epoxy from Epoxy Technology, Inc. of Billerica, Mass.) forms a domed structure on the tip of the pressure guidewire DRIE-Based Manufacturing Method A method is described that utilizes a combination of DRIE processing and lapping (to remove excess silicon from the mechanical substrate) or any other wafer thinning method to facilitate fabrication of a frame containing multiple sensor chips attached by thin, so that at no point is there a need to handle a thin, delicate wafer.

Silicon pressure sensors for this coronary guidewire application normally require a built-in reference chamber, since it is impractical to provide an atmospheric pressure reference inside the coronary artery. The reference chamber is typically formed by creating a sandwich of two silicon wafers or of a silicon wafer and a glass wafer. By way of example, a vacuum-filled chamber is formed by etching a well or depression in a first silicon wafer, then bonding that first silicon wafer to a second silicon wafer under vacuum using the silicon fusion bonding method. Subsequently, the first silicon wafer is thinned by grinding and etching in a known manner to leave just a thin membrane of silicon, the diaphragm, covering the pressure reference chamber. Silicon resistors implanted in the diaphragm prior to the wafer bonding stage now become pressure sensitive by virtue of their inherent sensitivity to strain created by pressure induced flexure of the thin diaphragm. Placement and orientation of the resistors according to well established principles can produce resistive elements having either positive or negative response to applied pressure. Once this wafer sandwich is formed with its myriad diaphragms, reference chambers, and piezoresistors, the pressure sensor fabrication is completed by adding metallized bonding pads and patterning the sensor outlines with DRIE.

In accordance with an exemplary method DRIE processing etches the sensor outlines for a set of sensor chip devices on a single silicon wafer (sandwich). In an exemplary embodiment, DRIE is carried out to a depth of approximately 100 µm. During DRIE processing, the wafer is still 400 µm thick, and relatively resistant to breakage. Next, the DRIE processed wafer is mounted in a lapping machine. By way of example, wax secures the wafer to a holder. The wafer is thereafter lapped in a known manner to remove excess wafer material. Once the device has been thinned to the DRIE depth (e.g., 100 µm) the set of solid-state sensor chip become separated from the bulk of the wafer (except for narrow breakable tabs), and are supported primarily by the wax matrix and the holder. Lapping continues until the desired device thickness is achieved (e.g., 75 µm). The individual pressure chip devices are thereafter freed from the holder by soaking in hot water or solvent to melt or dissolve the wax, leaving thin, individual pressure sensor devices behind, attached to a framework by narrow breakable tabs.

Illustrative embodiments of the present invention and certain variations thereof have been provided in the Figures and accompanying written description. Those skilled in the art will readily appreciate from the above disclosure that many variations to the disclosed embodiments are possible in alternative embodiments of the invention. Such modifications include, by way of example, modifications to the form of the disclosed circuitry and physical structures of the sensor chips and associated intravascular pressure sensor assembly components. The present invention is not intended to be limited to the disclosed exemplary embodiments. Rather the present invention is intended to cover the disclosed embodiments as well as others falling within the scope and spirit of the invention to the fullest extent permitted in view of this disclosure and the inventions defined by the claims appended herein below.

What is claimed is:

1. An intravascular physiologic sensing device, comprising:
    a flexible elongate member including a proximal end and a distal end, the flexible elongate member defining a longitudinal axis;
    a housing mounted at the distal end of the flexible elongate member; and
    a sensor chip extending in length completely within the housing, the sensor chip comprising:
    a surface;
    a widened portion;
    a cantilevered portion integrally formed with and extending distally from the widened portion along the length, wherein the surface comprises a first width at the widened portion and a smaller, second width at the cantilevered portion, wherein the first width and the second width extend laterally with respect to the longitudinal axis; and
    at least one physiologic sensing element disposed on the cantilevered portion.

2. The device of claim 1, wherein a distal end of the cantilevered portion comprises a rectangular outline.

3. The device of claim 1, wherein a distal end of the cantilevered portion comprises a non-rectangular outline.

4. The device of claim 1, wherein the at least one physiologic sensing element comprises a rectangular outline.

5. The device of claim 1, wherein the at least one physiologic sensing element comprises a non-rectangular outline.

6. The device of claim 1, wherein the housing comprises an opening configured to allow a fluid to exert pressure on the at least one physiologic sensing element.

7. The device of claim 6, further comprising a pressure-conveying material positioned within the housing and in direct contact with the at least one physiologic sensing element, wherein the pressure-conveying material is configured to allow a fluid to exert pressure on the at least one physiologic sensing element through the opening of the housing.

8. The device of claim 1, wherein the widened portion of the sensor chip comprises one or more notches configured to interface with an inner wall of the housing.

9. The device of claim 1, wherein the widened portion of the sensor chip comprises a non-rectangular edge adjacent to an inner wall of the housing.

10. The device of claim 1, wherein the sensor chip further comprises a plurality of contacts in electrical communication with the at least one physiologic sensing element via a plurality of lead lines, each of the plurality of lead lines extending between a respective electrical contact of the plurality of electrical contacts and the at least one physiologic sensing element.

11. The device of claim 10, further comprising a plurality of wires extending along a length of the flexible elongate member and in electrical communication with the at least one physiologic sensing element via the plurality of electrical contacts.

12. The device of claim 11, wherein the sensor chip further comprises at least one cutout sized and shaped to receive at least one of the plurality of wires.

13. The device of claim 12, wherein the sensor chip further comprises a plurality of cutouts, wherein each of the plurality of cutouts is sized and shaped to receive a respective wire of the plurality of wires.

14. The device of claim 13, wherein each cutout of the plurality of cutouts is positioned proximate to a perimeter of the sensor chip.

15. The device of claim 13, wherein each cutout of the plurality of cutouts are positioned adjacent to one another.

16. The device of claim 13, wherein the widened portion of the sensor chip includes at least one of the plurality of cutouts.

17. The device of claim 1, wherein the flexible elongate member is a guidewire.

18. The device of claim 1, wherein the cantilevered portion comprises a pressure-sensitive region on a first surface of the cantilevered portion, and wherein the at least one physiologic sensing element is contained within the pressure-sensitive region.

19. The device of claim 18, wherein the physiologic sensing element comprises a piezoresistive element configured to deflect relative to the cantilevered portion to detect a pressure of a fluid outside the housing.

20. The device of claim 1, wherein the physiologic sensing element comprises a chamber and a membrane positioned over the chamber, wherein the membrane is configured to deflect relative to the cantilevered portion.

21. The device of claim 1, wherein the widened portion substantially abuts an inner wall of the housing, the widened portion held in place within the housing by a holding material that surrounds the widened portion and not the physiologic sensing element.

22. The device of claim 1, further comprising a transition between the widened portion and the cantilevered portion, the transition comprising a third width extending from the first side of the sensor chip to the second side of the sensor chip, wherein the third width decreases along the transition from the widened portion to the cantilevered portion.

23. An intravascular physiologic sensor assembly, comprising:
    a sensor chip extending in length, wherein the sensor chip comprises:
        a surface;
        a widened portion;
        a cantilevered portion integrally formed with and extending distally from the widened portion along the length, wherein the surface comprises a first width at the widened portion and a smaller, second width at the cantilevered portion, wherein the first width and the second width extend laterally with respect to a longitudinal axis of the sensor chip; and
        at least one physiologic sensing element disposed on the cantilevered portion.

24. A method of manufacturing an intravascular physiologic sensing device, the method comprising:
    forming a sensor chip using photolithography in combination with deep reactive-ion etching (DRIE), the sensor chip extending in length, the sensor chip including:
        a surface;
        a widened portion;
        a cantilevered portion integrally formed with and extending distally from the widened portion along the length, wherein the surface comprises a first width at the widened portion and a smaller, second width at the cantilevered portion, wherein the first width and the second width extend laterally with respect to a longitudinal axis of the sensor chip; and
        at least one physiologic sensing element disposed on the cantilevered portion.

* * * * *